(12) United States Patent
Asrani et al.

(10) Patent No.: US 10,278,724 B2
(45) Date of Patent: May 7, 2019

(54) METHOD AND APPARATUS FOR GRAFTING OF SKIN TISSUE

(71) Applicant: THE GENERAL HOSPITAL CORPORATION, Boston, MA (US)

(72) Inventors: Falguni Asrani, Malden, MA (US); William Farinelli, Danvers, MA (US); Ajay Shah, Cambridge, MA (US); Vincent Liu, Cambridge, MA (US); Richard R. Anderson, Boston, MA (US)

(73) Assignees: The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 226 days.

(21) Appl. No.: 15/253,525

(22) Filed: Aug. 31, 2016

(65) Prior Publication Data
US 2017/0128096 A1    May 11, 2017

Related U.S. Application Data

(63) Continuation of application No. 13/120,799, filed as application No. PCT/US2009/058194 on Sep. 24, 2009, now Pat. No. 9,451,979.
(Continued)

(51) Int. Cl.
| | | |
|---|---|---|
| *A61B 17/322* | (2006.01) | |
| *A61F 2/10* | (2006.01) | |
| *A61B 17/00* | (2006.01) | |

(52) U.S. Cl.
CPC .......... *A61B 17/322* (2013.01); *A61F 2/105* (2013.01); *A61B 2017/00969* (2013.01); *A61B 2017/3225* (2013.01)

(58) Field of Classification Search
CPC ........ A61B 17/322; A61B 2017/00969; A61B 2017/3225; A61F 2/105
See application file for complete search history.

(56) References Cited

U.S. PATENT DOCUMENTS

| | | |
|---|---|---|
| 2,590,299 A | 3/1952 | Douglas |
| 3,782,387 A | 1/1974 | Falabella |
| (Continued) | | |

FOREIGN PATENT DOCUMENTS

| | | |
|---|---|---|
| WO | 2004078032 A2 | 9/2004 |
| WO | 2005067442 A2 | 7/2005 |
| (Continued) | | |

OTHER PUBLICATIONS

Awad, Chinese Cupping: A Simple Method to Obtain Epithelial Grafts for the Management of Resistant Localized Vitiligo, Dermatol. Surg., 2008, 34:1186-1193.
(Continued)

*Primary Examiner* — Christine H Matthews
*Assistant Examiner* — Joshua Daryl D Lannu
(74) *Attorney, Agent, or Firm* — Quarles & Brady LLP

(57) ABSTRACT

Methods and apparatus are provided for affecting an appearance of skin by harvesting small portions of tissue from a donor (first) site and applying them at a recipient (second) site. A plurality of micrografts can be formed from a piece of graft tissue and attached to a dressing material. The dressing material can then be expanded to increase a separation distance between the micrografts, and the dressing material having spaced-apart micrografts attached thereto can be applied to a prepared recipient site. An apparatus can be provided that expands the dressing material using a pressurized fluid. A further method can include providing a suspension of small portions of graft tissue in a solution. The solution can be injected into blisters formed at a recipient
(Continued)

(second) site and the tissue portions allowed to attach and proliferate. A method and apparatus can also be provided for forming corresponding blisters at a donor site and at a recipient site. The raised (removed) portions of the blisters can be removed and attached to a dressing material, and the portions from the donor (first) site can be placed onto the exposed blister areas at the recipient site.

24 Claims, 13 Drawing Sheets

Related U.S. Application Data

(60) Provisional application No. 61/153,846, filed on Feb. 19, 2009, provisional application No. 61/099,799, filed on Sep. 24, 2008.

(56) References Cited

U.S. PATENT DOCUMENTS

| | | | |
|---|---|---|---|
| 5,921,980 A | 7/1999 | Kim | |
| 6,071,247 A | 6/2000 | Kennedy | |
| 6,722,363 B1 | 4/2004 | Von Schuckmann | |
| 8,562,626 B2 | 10/2013 | Sabir et al. | |
| 8,617,181 B2 | 12/2013 | Sabir et al. | |
| D706,422 S | 6/2014 | Ziegler et al. | |
| 8,926,631 B2 | 1/2015 | Sabir et al. | |
| 8,978,234 B2 | 3/2015 | Sabir et al. | |
| D729,386 S | 5/2015 | Ziegler et al. | |
| D732,665 S | 6/2015 | Ziegler et al. | |
| 9,173,674 B2 | 11/2015 | Sabir et al. | |
| 9,414,856 B2 | 8/2016 | Sabir et al. | |
| 9,451,979 B2 | 9/2016 | Asrani et al. | |
| 2002/0124846 A1 | 9/2002 | Ekelius et al. | |
| 2003/0011859 A1 | 6/2003 | Paris et al. | |
| 2004/0176787 A1* | 9/2004 | Mishra | A61B 17/322 606/167 |
| 2006/0058842 A1 | 3/2006 | Wilke et al. | |
| 2006/0258956 A1 | 11/2006 | Haberstich et al. | |
| 2006/0282104 A1 | 12/2006 | Williamson, IV et al. | |
| 2007/0255168 A1 | 11/2007 | Hibner et al. | |
| 2008/0051822 A1 | 2/2008 | Widgerow | |
| 2009/0036795 A1 | 2/2009 | Duineveld et al. | |
| 2012/0035619 A1 | 2/2012 | Sabir et al. | |
| 2012/0197267 A1 | 8/2012 | Sabir et al. | |
| 2013/0145596 A1 | 6/2013 | Sabir et al. | |
| 2013/0204273 A1 | 8/2013 | Sabir et al. | |
| 2014/0277454 A1 | 9/2014 | Locke et al. | |
| 2015/0182241 A1 | 7/2015 | Pratt et al. | |
| 2015/0182242 A1 | 7/2015 | Pratt et al. | |
| 2015/0201954 A1 | 7/2015 | Pratt et al. | |
| 2015/0201955 A1 | 7/2015 | Sabir et al. | |
| 2015/0238212 A1 | 8/2015 | Sabir et al. | |
| 2016/0296663 A1 | 10/2016 | Higley et al. | |

FOREIGN PATENT DOCUMENTS

| | | |
|---|---|---|
| WO | 2007034438 A2 | 3/2007 |
| WO | 2010036788 A2 | 4/2010 |
| WO | 2012019094 A2 | 2/2012 |
| WO | 2012019095 A2 | 2/2012 |
| WO | 2012019096 A1 | 2/2012 |
| WO | 2012019098 A1 | 2/2012 |
| WO | 2012102812 A1 | 8/2012 |
| WO | 2013086400 A1 | 6/2013 |
| WO | 2014152319 A2 | 9/2014 |
| WO | 2014152346 A1 | 9/2014 |
| WO | 2015103041 A1 | 7/2015 |
| WO | 2015103043 A1 | 7/2015 |
| WO | 2015103045 A1 | 7/2015 |
| WO | 2016164890 A1 | 10/2016 |

OTHER PUBLICATIONS

Kreis, et al., Expansion Techniques for Skin Grafts: Comparison Between Mesh and Meek Island (Sandwich-) Grafts, Burns, 1994, 20(1):S39-S42.

Kreis, et al., Widely Expanded Postage Stamp Skin Grafts Using a Modified Meek Technique in Combination with an Allograft Overlay, Burns, 1993, 19(2):142-145.

Lari, et al., Expansion Technique for Skin Grafts (Meek Technique) in the Treatment of Severely Burned Patients, Burns, 2001, 27:61-66.

Meek, Successful Microdermagrafting Using the Meek-Wall Microdermatome, American Journal of Surgery, 1958, 96(4):557-558.

Mulekar, et al., Treatment of Vitiligo on Difficult-to-Treat Sites Using Autologous Noncultured Cellular Grafting, Dermatol. Surg., 2009, 35:66-71.

Srinivas, et al., Meshed Split Skin Graft for Extensive Vitiligo, Indian J. Dermatol. Venereol. Leprol., 2004, 70(3):165-167.

PCT International Search Report and Written Opinion, PCT/US2009/058194, dated Apr. 28, 2010.

* cited by examiner

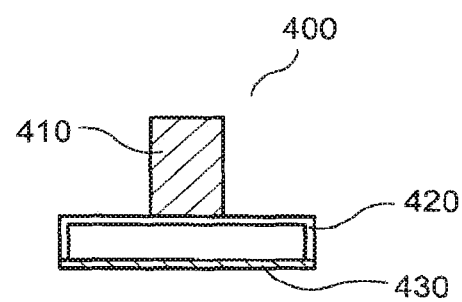
F I G. 4C
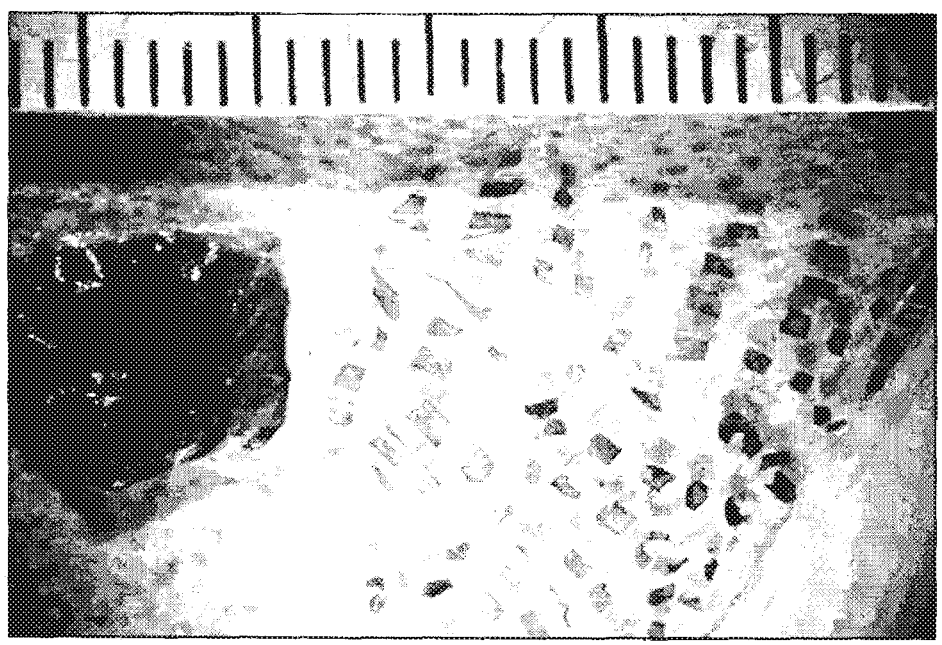
F I G. 5

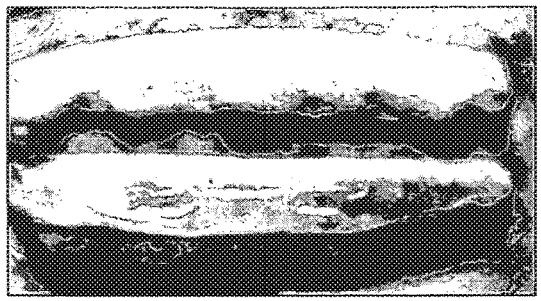 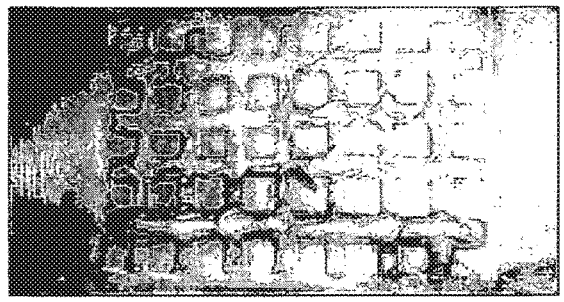
FIG. 10A  FIG. 10B
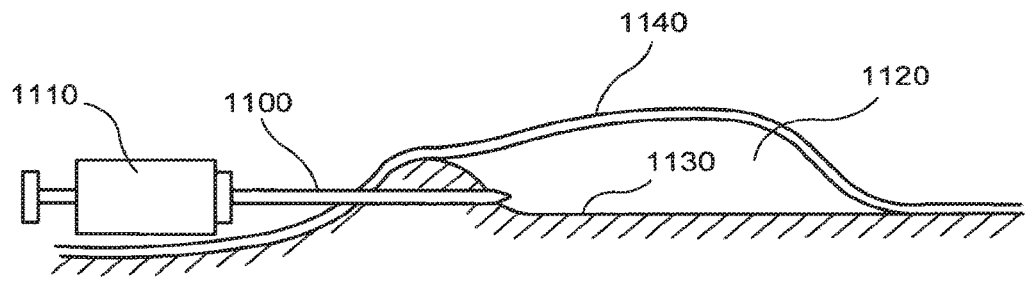
FIG. 11

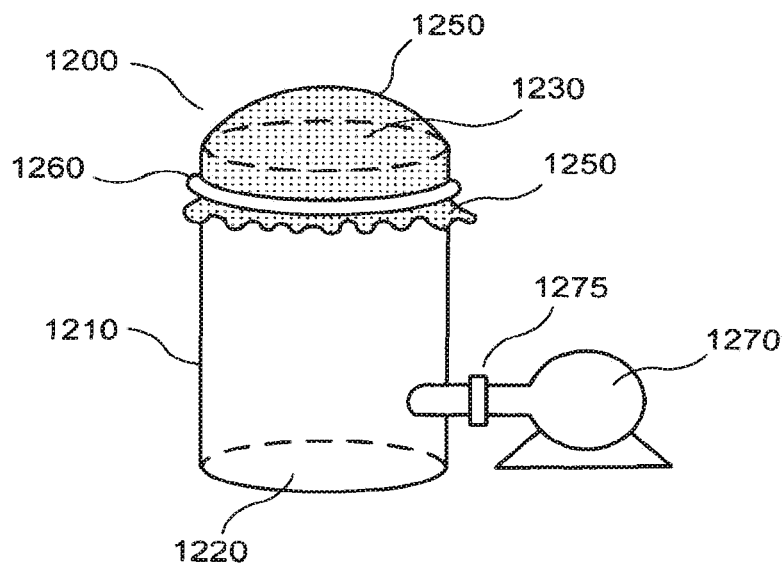
F I G. 12A
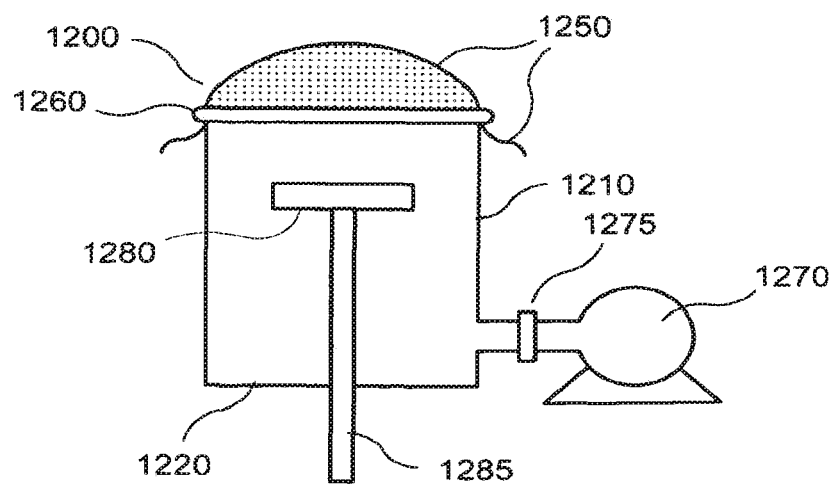
F I G. 12B

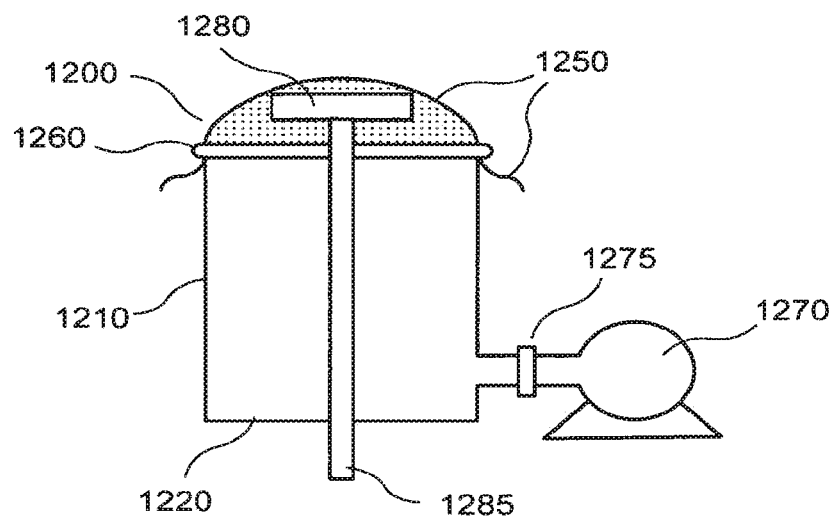
F I G. 12C
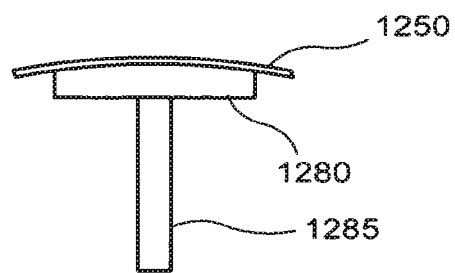
F I G. 12D

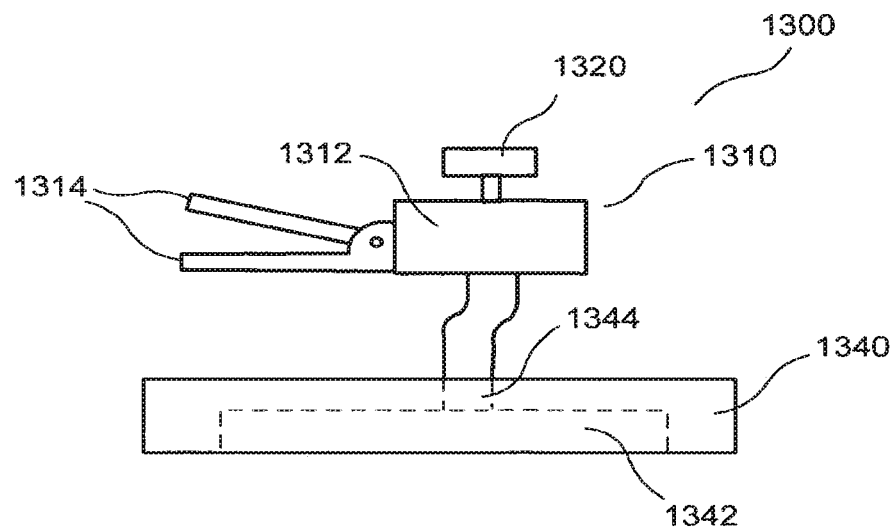
F I G. 13A
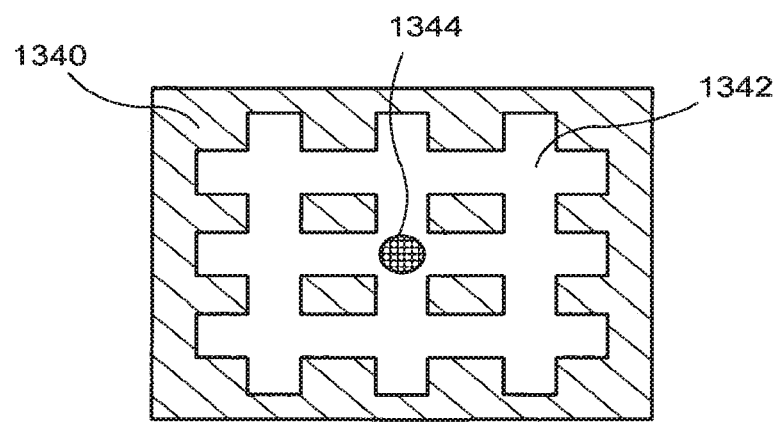
F I G. 13B

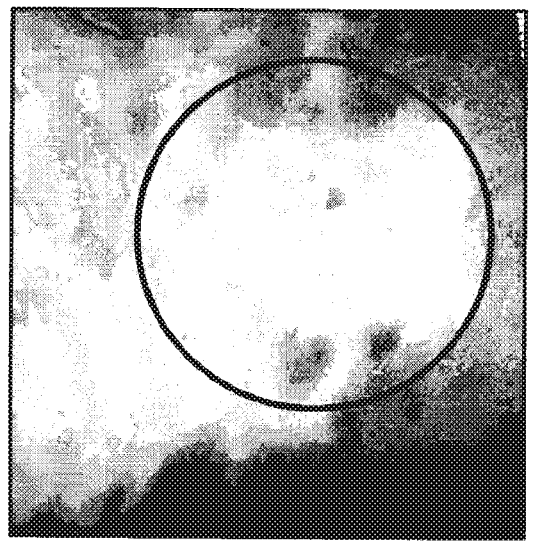
F I G. 17C
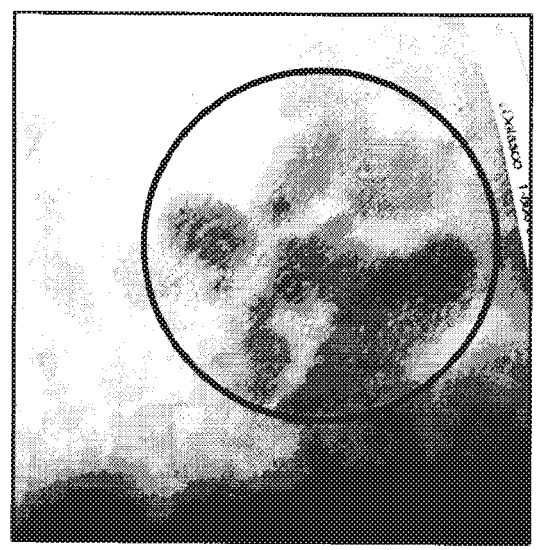
F I G. 17D

METHOD AND APPARATUS FOR GRAFTING OF SKIN TISSUE

CROSS REFERENCE TO RELATED APPLICATIONS

The present application is a continuation application of U.S. application Ser. No. 13/120,799 filed Jul. 11, 2011 which is a National Stage Entry of International Patent Application No. PCT/US2009/058194 filed Sep. 24, 2009, which claims priority from U.S. Provisional Patent Application Ser. No. 61/099,799 filed Sep. 24, 2008, and from U.S. Provisional Patent Application Ser. No. 61/153,846 filed Feb. 19, 2009, the disclosures of which are incorporated herein by reference in their entirety.

TECHNICAL FIELD

The present disclosure is directed to methods and apparatus for grafting of skin tissue using microscopic tissue grafts from a donor site.

BACKGROUND

Skin tissue may be subject to many forms of damage, including burns, trauma, depigmentation (e.g., vitiligo), and the like. Grafts are often used to repair such skin damage. However, grafting techniques generally involve a large amount of tissue being removed from a donor site, preferably from the patient, and/or expensive and complex cultivation procedures using laboratory facilities to form larger portions of graft tissue from smaller donor samples.

For example, many people exhibit a condition known as vitiligo which results in depigmented regions of skin that may be aesthetically undesirable. Such depigmentation can cause a psycho-social stigma, especially in darker skinned individuals. Vitiligo affects about 1-4% of the population, including an estimated 1 to 2 million Americans. It affects both males and females of all races and ages.

Melanin is a pigment which gives skin its characteristic color. It is produced by certain skin cells called melanocytes. Vitiligo results when melanocytes either die or stop producing melanin. This condition may begin as small patches of lightened or whitened skin that can spread and grow larger with time. The depigmentation may occur cyclically, with periods of no change followed by periods of further pigment loss. The regions of depigmented skin tend to be irregular, and are more noticeable on people having darker skin. The exact cause of vitiligo is presently unknown, but it is believed to be associated with an autoimmune reaction.

Stable vitiligo generally refers to a vitiligo condition in which the lesions are not noticeably increasing in size or number over an extended observation period (e.g., days or weeks or longer). Present treatments for stable vitiligo have limited effectiveness. Such treatments can include oral medications or topical creams containing corticosteroid compounds. Ultraviolet therapy based on exposure to, e.g., UV-A or UV-B radiation combined with application of psoralen (a photosensitizer) may also be used. Temporary darkening of the depigmented areas can also be achieved by application of tinted cosmetics or dyes that color the skin. Another option is to permanently remove pigment in the surrounding normally-pigmented skin to achieve homogenous skin tone is possible by topical application of a compound containing 20% monobenzyl ether of hydroquinone. This therapy generally takes about a year to complete, and the pigment removal is permanent.

Autografting procedures in which a patient's own melanocytes are applied to the depigmented areas are another treatment technique for vitiligo. Culturing of melanocytes and transplanting them to depigmented areas can result in uniform repigmentation, but such autografting techniques can be cumbersome, expensive, time-consuming and/or require advanced laboratory facilities. A recent commercial version of this approach uses a harvesting device and bioenzymes to disperse melanocytes prior to autografting. This treatment can be expensive and often introduces enzymes which may not be desirable.

Sheet grafts can provide an improved appearance of the repaired tissue site and have been used, for example, to treat vitiligo. For example, sheet grafts may be used on large areas of the face, neck and hands, so that these more visible parts of the body can appear less scarred after healing. A sheet graft may be used to cover an entire depigmented or damaged region of skin, e.g., if the damaged site is small. Small areas of a sheet graft can be lost after placement because a buildup of fluid (e.g., a hematoma) can occur under the sheet graft following placement the sheet graft.

Sheet grafts may be full-thickness or split-thickness. A conventional split-thickness graft can be formed, e.g., by harvesting a sheet of epidermis and upper dermal tissue from a donor site, in a procedure similar to that of peeling an apple. The split-thickness graft can then be placed on the location of the burn or ulcer. The skin tissue may then grow back at the donor site following a generally extended healing time. Split-thickness grafts may be preferable to full-thickness grafts because removing large amounts of full-thickness skin tissue from the donor site can lead to scarring and extensive healing times at the donor site, as well as an increased risk of infection. However, skin tissue removed from the donor site for a split-thickness skin autograft may include both the epidermis and a portion of the dermis, which can lead to some scarring and/or dispigmentation (e.g., hyper- or hypo-pigmentation) at the donor site.

Another conventional technique that may be used to treat skin pigmentation defects can be referred to as "non-cultured autologous melanocyte transplantation." In this technique, harvested graft tissue can be dissociated using either an enzymatic digestion process (e.g., by treating the tissue with trypsin or the like), or by mechanically grinding the tissue to form a paste-like substance. The resulting cell solution can then be transplanted onto a dressing (e.g., a conventional dressing, a collagen bandage, etc.) and the dressing then applied to the affected area. However, grafts formed using such techniques may not be well-controlled and/or reproducible. Processing of the graft tissue in such techniques can also produce cellular trauma, which can reduce the effectiveness of the applied grafts.

Burns are another common form of skin trauma which may be treated by autografting. Large areas of skin may be damaged by burns, which generally require removal of larger areas of tissue from donor sites to repair them. Repair of burned tissue is often based on providing tissue containing viable keratinocytes to the burned area. Proliferation of the keratinocytes can help to regrow skin tissue and repair the damaged areas.

Another autografting approach is blister grafting, in which blisters are created on pigmented skin using suction. The raised blisters are then cut off and transplanted to depigmented skin areas, where blisters of the same size have been formed and removed. This technique generally requires the extensive use of donor sites having substantially the same area as the depigmented regions being treated. An exemplary blister grafting technique, in which small graft strips formed from raised blisters are transferred to a dermabraded recipient site, is described in S. S. Awad, *Dermatol Surg,* 34:9 (September 2008), 1186-1193. The Awad article also describes various devices used to form suction blisters.

Another autografting technique is "mini-punch" autografting, where mini-punch biopsies are taken from the donor area. Same-sized mini-punch biopsies are taken from the recipient depigmented sites and replaced by the donor area mini-punch grafts. This technique often results in a "cobblestone" appearance at the recipient site, and also may result in some scarring at the donor site. Mini-punch autografting may also not be effective for repigmenting large areas.

Still another conventional technique that may be used for autografting of tissue, often referred to in the literature as the "Meek technique," includes removal of a region of graft tissue from a donor site, cutting the graft tissue into micrografts—each having a size on the order of millimeters, applying the cut graft tissue onto a piece of prefolded gauze, and unfolding the gauze to separate the individual micrografts by a desired separation distance. The expanded gauze containing the separated micrografts can then be applied to a wound site to allow the micrografts to grow into the tissue at the wound site. After several days, the gauze may be removed and an allograft overlay or the like can be applied over the micrografts. Such technique is described, e.g., in R. W. Kreis et al., *Burns,* 20 (1) (1994), S39-S42, and in A. R. Lari et al., *Burns,* 27, (2001), 61-66. The Meek technique can be limited by the relatively large size of the micrografts used, which may lead to a nonuniform appearance of the skin, and the use of gauze that is prefolded in a particular configuration that determines the subsequent separation distances of the micrografts.

Another autografting technique, described in S. V. Mulekar et al., *Dermatol Surg,* 35:1 (January 2009), 66-71, includes formation of a centrifuged suspension of cells obtained from a superficial portion of a donor site. This suspension is then applied over a larger recipient site that has been abraded, and then covered with a dry collagen film.

Accordingly, there is a need for improved methods and apparatus for repairing skin tissue, such as treating vitiligo by repigmenting regions of skin or healing burns, which is long-lasting, relatively simple and inexpensive, and effective. Such methods and apparatus preferably do not require enzymes or expensive and complex laboratory facilities and cell cultures, and would preferably be capable of repairing relatively large areas of tissue without needing removal of large portions of skin from donor sites.

SUMMARY

Such needs can be addressed with the exemplary embodiments of the present disclosure as described herein.

For example, exemplary embodiments of the present disclosure relate to method and apparatus for providing repair, including repigmentation, of damaged regions of skin tissue that may be significantly larger than the area of tissue removed from donor sites. Such exemplary repair can be performed in a clinical setting using mechanical procedures that do not require cell cultures, enzymes, or specialized laboratory facilities. Exemplary embodiments of the present disclosure are relatively simple and inexpensive when compared to existing autografting techniques.

In a first exemplary embodiment, methods can be provided for repairing damaged tissue that include obtaining a portion of donor tissue, e.g., full-thickness epidermal tissue, which can be obtained using any of several techniques, e.g., forming a suction blister at a donor site. The donor tissue can then be divided up into small pieces of individual graft tissue having, for example, a lateral dimension less than about 1 mm, e.g., about 200-1000 microns, or preferably between about 400-800 microns. These pieces of graft tissue (e.g., micrografts) can then be adhered to a pliable dressing material, and the dressing material expanded to provide a spaced-apart array of micrografts. The micrografts and dressing material can be applied directly to a prepared recipient site, such that the micrografts contact the tissue at the recipient site and may attach thereto and grow.

In a second exemplary embodiment of the present disclosure, a cutting apparatus can be provided that is configured to form a plurality of micrografts from a piece of graft tissue. A frame and/or handle may optionally be provided to facilitate manipulation of the apparatus. The exemplary apparatus can include a plurality of substantially parallel blades or cutting edges spaced less than about 1 mm apart, e.g., about 200-1000 microns apart, or preferably between about 400-800 microns apart. The cutting edges can be pressed into the graft tissue at least twice, in different orientations, to form small micrografts from the graft tissue. In a further exemplary embodiment, the cutting edges can be provided in the form of a fine mesh, where the width of the openings in the mesh are less than about 1 mm wide, e.g., about 200-1000 microns wide, or preferably between about 400-800 microns wide.

In a third exemplary embodiment of the present disclosure, a stretching apparatus can be provided that can be used to controllably stretch or expand a dressing material having micrografts adhered thereto, to produce a larger separation distance between individual micrografts. The exemplary stretching apparatus can include a housing having an interior volume and an open end configured to receive a piece of dressing material. A pressure source and, or valve arrangement may be provided in communication with the housing. The exemplary stretching apparatus can be configured to expand the dressing material based on, e.g., a force provided by a pressurized gas or other fluid introduced into the interior volume of the apparatus. A substrate may be provided that is movably or slideably connected to the housing, such that the substrate can be brought into contact with a portion of the dressing material while it is expanded.

In a fourth exemplary embodiment, a suction apparatus can be provided that may be used to form a network or plurality of suction blisters in various configurations on a region of skin. The geometry of such exemplary configurations can be selected to facilitate substantially uniform repigmentation of the region of skin when melanocytes are provided within the blisters. For example, the suction exemplary apparatus can include a plate having one or more channels provided on a surface thereof. A passageway can be provided between each channel and an external portion of the plate that is configured to be attached to a source of low pressure or vacuum. The distance between adjacent channels can be less than 4 mm, or less than about 2 mm. The channels can be configured as a plurality of elongated grooves, or optionally as an intersecting network of such grooves. A width of each channel may be less than about 10 mm wide, or less than about 5 mm wide.

In a fifth exemplary embodiment, method and apparatus can be provided for forming a plurality of blisters at predetermined locations at a donor site and at a recipient site. An upper portion of the blisters can optionally be removed from both sites, exposing areas of skin beneath the removed blisters. The portions of blister tissue removed from the donor site can be placed on matching areas of exposed skin tissue at the recipient site using a dressing material. Optionally, the removed pieces of blister tissue from the recipient site can similarly be placed over corresponding exposed areas of skin at the donor site. An apparatus can be provided that includes a plate having a plurality of holes provided therethrough to facilitate formation of the plurality of blisters. The apparatus can optionally include one or more spacers configured to position the plate away from the tissue surface, such that a cutting blade or the like can be traversed between the plate and tissue surface to sever the raised portions of the blisters. A further plate having holes corresponding to (and aligned with) the holes in the first plate can be affixed to and slightly spaced apart from the first (upper) plate such that a portion of the raised blisters pass through the corresponding holes in both plates. A blade or other cutting arrangement can be traversed between the plates to sever the raised portions of the blisters. Alternatively, the lower plate may be slidably attached to the upper plate. The lower plate can be thin and/or provided with sharp edges around the holes, such that the raised portions of the blisters are severed from the underlying tissue when the lower plate is translated with respect to the upper plate.

In a sixth exemplary embodiment, a method for repairing damaged tissue can be provided that include obtaining a portion of donor tissue, e.g., full-thickness epidermal tissue, which can be obtained using any of several techniques such as forming a suction blister at a donor site. The donor tissue can then be divided up into small portions of graft tissue that can then be introduced into a solution to form a suspension. The suspension containing the portions of graft tissue can be injected under one or more blisters formed at the recipient such that the portions of tissue may contact and adhere to the skin beneath the blister at the recipient site and grow. The suspension may be injected into the lower portion of the raised blister through adjacent tissue to allow the raised blister to remain intact, thus enclosing the injected suspension and tissue portions within the blister.

These and other objects, features and advantages of the present disclosure will become apparent upon reading the following detailed description of embodiments of the invention, when taken in conjunction with the appended claims.

BRIEF DESCRIPTION OF DRAWINGS

Further objects, features and advantages provided by the present disclosure will become apparent from the following detailed description taken in conjunction with the accompanying figures showing illustrative embodiments, in which:

FIG. 4C is a schematic side view of an exemplary mesh apparatus that can be used to form micrografts;

FIG. 5 is an image of the micrografts shown in FIG. 3B adhered to a dressing material that is subsequently stretched;

FIG. 10A is an image of an exemplary blister patterns that can be used to provide an exemplary repigmentation of an area of skin;

FIG. 10B is an image of a further exemplary blister patterns that can be used to provide an exemplary repigmentation of an area of skin;

FIG. 11 is a schematic side view illustrating an introduction of a needle into a suction blister without piercing the raised tissue above the blister in accordance with exemplary embodiments of the present disclosure;

FIG. 12A is a schematic illustration of an exemplary apparatus that can be used to controllably stretch a dressing material having micrografts adhered thereto;

FIG. 12B is a schematic illustration of a further exemplary apparatus that can be used to controllably stretch a dressing material, which includes a movable substrate that can be positioned in contact with the stretched dressing material;

FIG. 12C is a schematic illustration of the exemplary apparatus shown in FIG. 12B, with the substrate positioned in contact with the stretched dressing material;

FIG. 12D is a schematic illustration of the substrate with a portion of the stretched dressing material adhered thereto;

FIG. 13A is a schematic side view of an exemplary apparatus that can be used to form a plurality or network of suction blisters;

FIG. 13B is a schematic bottom view of the exemplary apparatus shown in FIG. 13A;

FIG. 17C is an exemplary image of a the recipient site before treatment, showing depigmented areas; and FIG. 17D is an exemplary image of the recipient site shown in FIG. 17C six weeks after treatment, showing repigmentation of depigmented areas.

DETAILED DESCRIPTION OF EXEMPLARY EMBODIMENTS

The present disclosure relates to exemplary methods and apparatus for repairing skin using autograft tissue, and particularly such exemplary methods and apparatus that may not require large areas of donor tissue and that are relatively easy and inexpensive to perform and use in a clinical setting. Such exemplary methods and apparatus can be used to repair skin damaged by burns, including both thermal and chemical burns, blistering, dermatological conditions such as epidermolysis bullosa or pyoderma gangrenosum, radiation therapy ulcers, diabetic ulcers, ischemic ulcers or trophic ulcers, trauma, or depigmentation (e.g., vitiligo).

Figure 1:
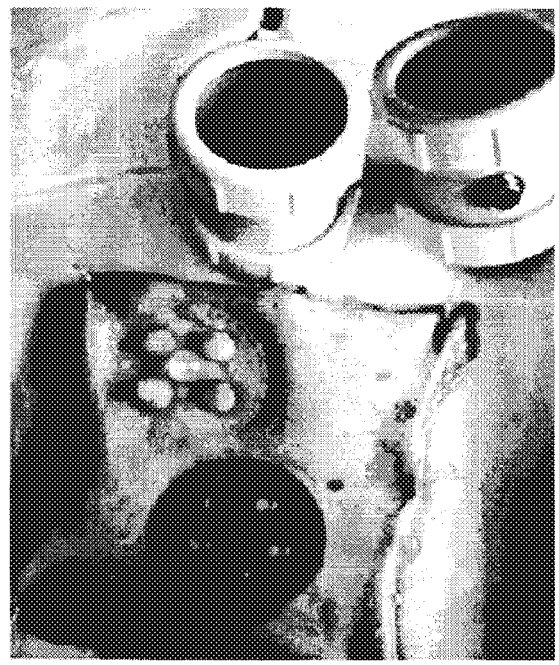
FIG. 1 is an image of a plurality of exemplary suction blisters being formed at a donor site to produce graft tissue.

In one aspect, exemplary embodiments of the present disclosure can provide a method for repairing or repigmenting skin tissue using autografts, where tissue harvested from donor sites can be used to repair or repigment areas of tissue that are larger than the donor sites. A plurality of raised blisters can be formed at a donor site, as shown in FIG. 1. These blisters can be formed as suction epidermal blisters. A conventional suction blister device can be used, which can include a hand vacuum pump, pressure control and/or temperature control. For example, suction blisters can be formed after a slight heating of the tissue, e.g., to a temperature of about 40-41° C. The diameters or lateral dimensions of the blisters can be between about 6 mm and about 12 mm, although larger or smaller blister sizes may be used.

Figure 2:
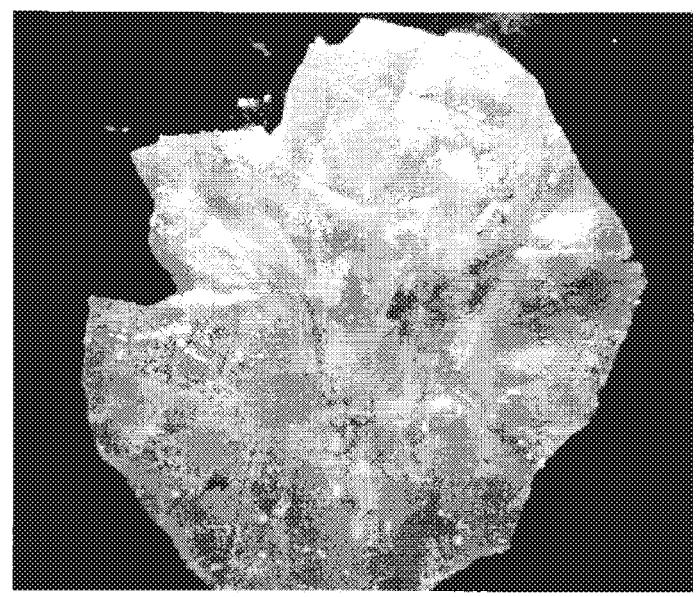
FIG. 2 is an image of a piece of graft tissue formed by removing a suction blister at a donor site.

The raised epidermal tissue of the blisters, which generally contains melanocytes, can be removed from the donor site by cutting. This graft tissue may then be placed on a glass slide or other sterile surface, for example with the stratum corneum (outer skin surface) facing up, as shown in FIG. 2.

The graft tissue can then be divided or minced, e.g., by making cuts or using other similar techniques, to form a plurality of micrografts form the graft tissue. The cuts may pass partially or completely through the graft tissue. For example, when repigmenting skin tissue, the micrografts used may preferably have a presence of melanocytes. Accordingly, a lateral dimension of such micrografts can be between less than about 1 mm, e.g., about 200-1000 microns, or preferably between about 400-800 microns. The area of the micrografts can be between about 0.04 mm$^2$ and about 1 mm$^2$, or more preferably between about 0.16 mm$^2$ and about 0.64 mm$^2$. These exemplary size ranges can provide micrografts large enough such that each micrograft is likely to contain some melanocytes, yet small enough to provide a large number of micrografts from a particular piece of graft tissue, which can facilitate a significant degree of expansion on the graft site as described herein. For treating burns or ulcers, where presence and proliferation of keratinocytes can be important, the micrograft sizes may be somewhat smaller. For example, a lateral dimension of micrografts containing keratinocytes can be between about 50 microns and about 1000 microns, or preferably between about 100 microns and about 800 microns. The area of such micrografts can be between about 0.0025 mm$^2$ and about 1 mm$^2$, or preferably between about 0.01 mm$^2$ and about 0.36 mm$^2$. These exemplary size ranges can provide micrografts large enough to contain viable and undamaged keratinocytes, and small enough to provide a large number of such micrografts from a particular piece of graft tissue to facilitate repair of a larger area of damaged skin.

Figure 3A:
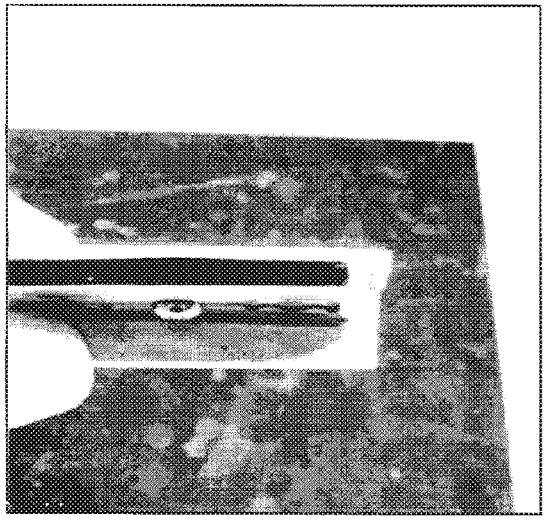
FIG. 3A is an image of an exemplary apparatus comprising a plurality of blades which can be used to form micrografts.
Figure 3B:
FIG. 3B is an image of exemplary micrografts formed using the exemplary apparatus shown in FIG. 3A.

In one exemplary embodiment, the micrografts can be formed using an apparatus that includes a plurality of substantially parallel, closely-separated blades, e.g., as shown in FIG. 3A. The distance between adjacent blades in this apparatus can be between about 200-1000 microns, or preferably between about 400-800 microns. This exemplary apparatus can be pressed onto the graft tissue to form a first plurality of substantially parallel cuts therethrough. The exemplary apparatus can then be pressed into the graft tissue a second time to form a second plurality of substantially parallel cuts, which may be substantially orthogonal to, or oriented at some angle with respect to, the first plurality of cuts. Exemplary micrografts formed by the cutting apparatus shown in FIG. 3A are shown in FIG. 3B.

Figure 4A:
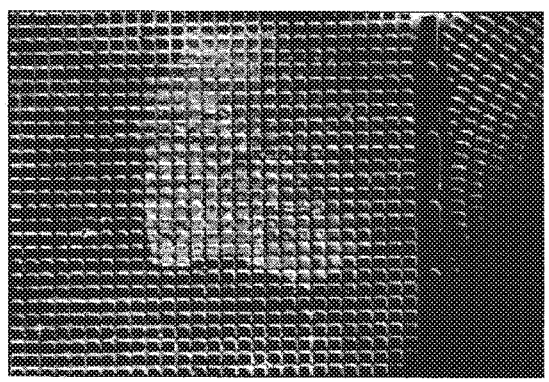
FIG. 4A is an image of an exemplary meshing apparatus placed over a piece of graft tissue to form micrografts in accordance with exemplary embodiments of the present disclosure.
Figure 4B:
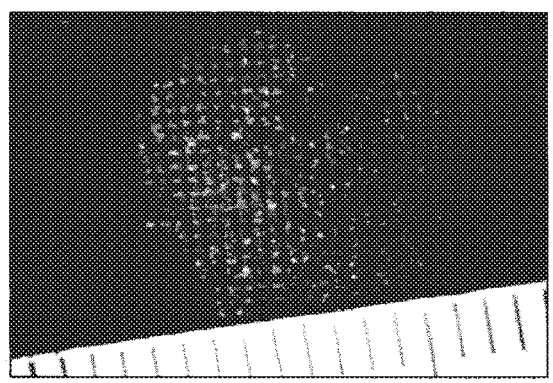
FIG. 4B is an image of exemplary micrografts formed from the graft tissue shown in FIG. 4A.

In a further exemplary embodiment, the micrografts can be formed using an exemplary mesh apparatus, such as that shown in FIG. 4A. The mesh apparatus can be pressed into the graft tissue to cut substantially through the graft tissue and form a plurality of micrografts. Exemplary micrografts formed using the mesh apparatus of FIG. 4A are shown in FIG. 4B.

The exemplary mesh apparatus can be formed, e.g., using a structurally rigid material that is not harmful to biological tissue such as a stainless steel or the like. For example, the exemplary mesh apparatus can be formed using a 316L stainless steel, or using another metal or metal alloy that may also be used to form surgical instruments. The exemplary mesh apparatus can include as a plurality of openings provided in a thin sheet of the mesh material. Such exemplary configuration may be less likely to trap pieces of tissue than, e.g., a woven screen configuration (e.g., a mesh having wires or strands of material woven together in orthogonal directions), and can facilitate separation of the micrografts from the exemplary apparatus.

The openings or holes provided in the exemplary mesh apparatus can be sized to provide micrografts in the desired size range. For example, the openings can have lateral sizes (e.g., opening widths or diameters) between about 100 microns and about 600 microns, or preferably between about 200 microns and about 400 microns. The width of the mesh material between these openings can be preferably small, e.g., less than about 100 microns. Smaller widths can be preferable to facilitate cutting and/or separation of the graft tissue after the exemplary mesh apparatus is pressed into the tissue. The width of the mesh material between the openings should also be sufficiently large to provide mechanical stability and not break or rupture when the exemplary mesh apparatus is pressed into the graft tissue.

The thickness of the exemplary mesh apparatus (e.g., the thickness of the sheet of material from which the mesh apparatus is formed) can preferably be about the same as or greater than the thickness of the graft tissue sample. Such mesh thickness can facilitate the exemplary mesh apparatus to be easily pressed down onto the graft tissue to divide it into micrograft pieces without having the graft tissue and/or micrografts formed therefrom protruding above an upper surface of the exemplary mesh apparatus. Such thickness can facilitate application of a press (e.g., a mechanical or hydraulic press) to the mesh surface to push the mesh through the graft tissue and divide it into a plurality of micrografts. For example, the thickness of an exemplary mesh can be greater than about 100 microns, e.g., between about 100 microns and about 250 microns. A stack of two or more thinner meshes can also be used, for example, where the total thickness of the stack can be greater than the thickness of the tissue being cut. The thickness of the stack can be, e.g., greater than about 100 microns, e.g., between about 100 microns and about 250 microns.

The openings in the exemplary mesh apparatus and the micrografts formed using this exemplary apparatus, shown in FIGS. 4A and 4B respectively, can be substantially square in shape. Further exemplary embodiments of the mesh apparatus can include mesh openings having other shapes, including elongated rectangular shapes, triangular shapes, honeycomb shapes (i.e., hexagons), or narrow diamondlike shapes. The shapes of such openings can be used to form micrografts having substantially similar shapes when the mesh apparatus is pressed into the graft tissue as described herein.

An exemplary embodiment of the mesh apparatus 400 can further include a handle 410, a frame 420, and/or additional material provided along one or more lateral sides of the mesh 430, as shown in FIG. 4C. For example, a rigid frame 420 can be attached to a peripheral portion of the mesh 430. The mesh 430 can be provided in tension when attached to the frame 420 to increase the structural rigidity of the mesh 430. Such exemplary features can facilitate manipulation of the mesh apparatus 400, including pressing of the mesh 430 into the graft tissue and removal of the mesh 430 therefrom.

In further exemplary embodiments of the present disclosure, cuts or indentations provided in the graft tissue to form micrografts, e.g., using the exemplary blade apparatus or exemplary mesh apparatus described herein, may not pass completely through the graft tissue. For example, such cuts or indentations can be provided such that a thin layer of substantially continuous tissue remains at a bottom portion of the graft tissue. Such thin layer can be provided by adjusting the pressure or force used to press the blade apparatus or mesh apparatus onto the upper portion of the graft tissue. A substantially continuous layer of tissue can facilitate (i) removal of the micrografts from an apparatus used to form them, (ii) manipulation of the small micrografts, and/or (iii) attachment of the micrografts to a dressing as described below. Individual micrografts can then be separated from one another along the cuts or indentations by applying a lateral force between them, as described herein. After micrografts are formed from the graft tissue, a dressing material can be placed over the micrografts such that the dressing material at least partially adheres to an upper surface (e.g., the stratum corneum) of the micrografts. Alternatively, a piece of dressing material can be provided on a surface with an adhesive surface facing upward. A piece of graft material can be placed on the dressing material such that the stratum corneum faces downward and contacts and adheres to the dressing material. Micrografts can then be formed, e.g., using an exemplary apparatus that can include a plurality of blades or a mesh apparatus, while the graft material is adhered to the dressing material.

The dressing material can be provided as a film, which can be biocompatible and capable of being stretched upon application of a moderate tensile force, and which may also be gas permeable. The dressing material can include a surface having adhesive properties on one side. For example, the dressing material may comprise Tegaderm™ dressing, Opsite™ dressing, or the like. The dressing material may have intrinsic adhesive properties, or alternatively a side of the dressing material can be treated with an adhesive material, e.g., an adhesive dressing spray such as Leukospray® (Beiersdorf GmbH, Germany).

The dressing material (e.g., Tegaderm™ dressing) having the micrografts adhered thereto can then be stretched to increase the distances between adjacent ones of the attached micrografts. If the micrografts are formed with a substantially continuous thin layer of tissue along one surface thereof, as described herein, stretching of the dressing material can also facilitate a separation of the micrografts. For example, lateral forces produced between individual micrografts, e.g., by stretching of the dressing material, can preferentially tear portions of the substantially continuous thin layer of tissue, if present, to separate the micrografts along the previously-formed cuts or indentations. The stretching can be done by hand or using an exemplary device configured to stretch the dressing material to a particular size. For example, the dressing material can be stretched by pulling it taut over a frame or smooth surface such as a mandrel, etc.

In a further exemplary embodiment of the present disclosure, an exemplary apparatus can be provided that facilitates substantially uniform stretching of the dressing material having micrografts adhered thereto, using a pressurized fluid such as a gas. Such exemplary apparatus is described in more detail herein below.

For repigmentation of skin tissue, the amount of stretching can be applied to the dressing material such that the distance between adjacent micrografts may be less than about 4 mm. Melanocytes, when grafted to the depigmented region, can migrate up to about 2 mm from each micrograft to repigment the regions between the micrografts. The distances between adjacent micrografts may be more preferably less than about 2 mm to provide more uniform repigmentation. Any minimum distance can be provided between micrografts after the dressing material is stretched. The amount of stretching can preferably be large enough to provide a sufficiently large area of dressing material containing micrografts to allow a larger area of damaged tissue to be repaired using a particular amount of graft tissue removed from the donor site. For example, the distance between adjacent micrografts on the stretched dressing material can be greater than about 0.5 mm, although smaller separation distances may also be used.

The amount of area expansion, e.g., the ratio of an area of damaged tissue that can be repaired to an area of graft tissue removed from a donor site, may be about 500× or more. An area expansion between about 10×-100× can be preferable in certain exemplary embodiments to provide a more uniform coverage and/or repigmentation of the recipient site. For repairing burns or ulcerated tissue, the micrografts may be somewhat smaller, as described above, and the separation distances between adjacent micrografts may be somewhat greater after stretching of the dressing material based on the greater migration range of keratinocytes. In such exemplary applications, an area expansion of about 1000× or more may be used.

Figure 6:
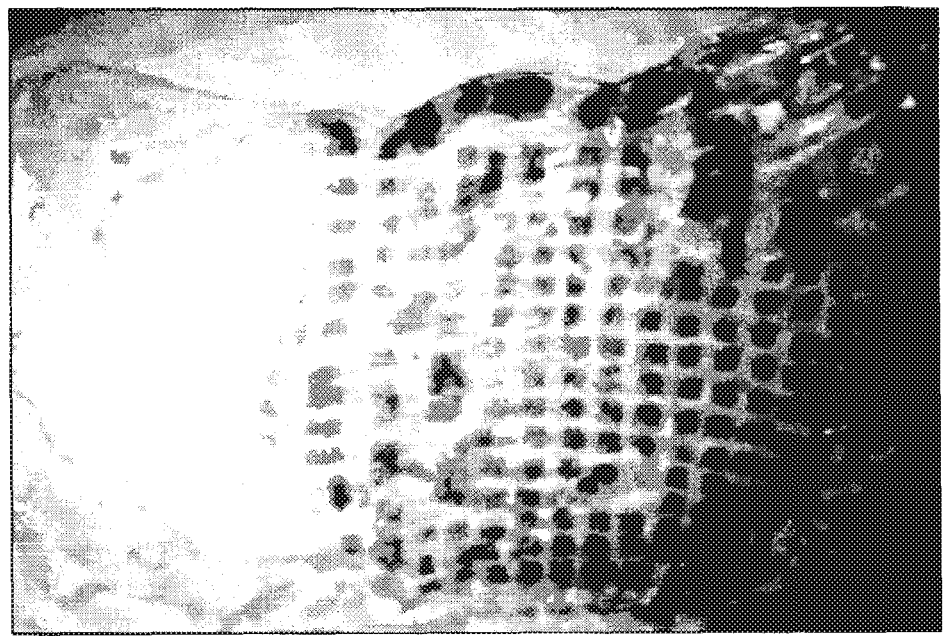
FIG. 6 is an image of micrografts shown in FIG. 4B adhered to a dressing material that has been subsequently stretched.

FIG. 5 shows an exemplary dressing material containing micrografts formed using the exemplary apparatus of FIG. 3A. The exemplary dressing material as shown in FIG. 5 has been stretched as described herein to separate the micrografts and expand the distance between adjacent micrografts. A piece of uncut graft tissue is shown to the left of the stretched dressing in FIG. 5. A similar piece of stretched dressing material having micrografts adhered thereto that were formed using the exemplary mesh apparatus shown in FIG. 4A, is shown in FIG. 6. The exemplary stretched dressing materials shown in FIGS. 5 and 6 support an array of spatially separated micrografts. As shown in FIG. 5 and described herein, the area of the stretched dressing material containing the separated micrografts can be much larger than the total area of the original uncut graft tissue.

Epidermal tissue, if present in the area to be treated, can be removed to prepare the area for receiving the micrografts. Burned or ulcerated areas may not need removal of epidermal tissue, although some cleaning of the area or other preparation of the recipient site may be performed. The size of the area where epidermal tissue has been removed at the recipient site can be about the same size as the area of the stretched dressing material having micrografts adhered thereto. This size can be greater than the area of the original graft tissue that was removed from the donor site to form the micrografts. The depigmented or damaged skin area to be treated can be dermabraded with sandpaper or another rough material. Alternatively, the epidermal tissue can be removed from the recipient site by forming one or more blisters over the area to be treated, e.g., a suction blister or a freezing blister, and the raised epidermal blister tissue can then be removed by cutting or another procedure. Suction blisters may be preferred for preparing recipient sites because they can produce less damage in the underlying tissue than other techniques such as abrading.

Figure 7:
FIG. 7 is an image of an exemplary stretched dressing material having micrografts adhered thereto that is placed over an area of skin to be repigmented.

The stretched dressing material can be placed over the area to be treated to form a dressing, as shown in the exemplary image of FIG. 7. A portion of the dressing material having micrografts adhered thereto can be positioned over the area to be repaired, e.g., the area from which the epidermal tissue has been abraded or removed for repigmentation. The stretched dressing material can be fixed in place over the treatment area, e.g., using tape or the like. The dressing material can be removed after sufficient time has elapsed to allow attachment and growth of the micrografts in the treatment area, e.g., after about 1-2 weeks. Optionally, the treatment area can then be exposed to UV-B radiation to promote formation of melanin in the treated area for repigmentation procedures.

This exemplary micrografting method can facilitate a repigmentation of an area of skin that can be much larger than the area of graft tissue removed from the donor site, e.g., 25× larger or more. Other exemplary degrees of expansion can be used by varying the amount of stretching of the dressing material. However, the amount of stretching is preferably small enough to produce a uniform appearance of the treated area after healing has occurred.

In another aspect, exemplary embodiments of the present disclosure can provide a further method for repigmenting skin tissue using autografting techniques. For example, one or more raised blisters of epidermal tissue can be formed at a donor site, as described above and shown in FIG. 1. The diameter of the blisters can be between about 6 mm and about 12 mm, although larger or smaller blister sizes can also be used. The raised epidermal tissue of a blister can be removed from the donor site by cutting or by another technique. This removed graft tissue can then be placed on a glass slide or other sterile surface with the stratum corneum facing down, such that the basal layer of the epidermal tissue is facing up.

Figure 8A:
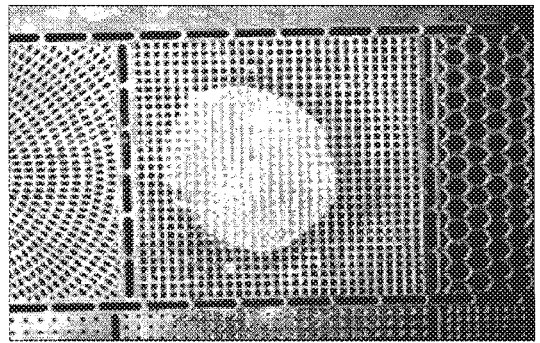
FIG. 8A is an image of an exemplary mesh apparatus placed over a piece of graft tissue in accordance with exemplary embodiments of the present disclosure.

A further exemplary mesh apparatus, similar to that shown in FIG. 4A, can then placed over the graft tissue, as shown in FIG. 8A. The exemplary mesh provided in this further mesh apparatus mesh can be thinner than the thickness of the graft tissue. For example, a sheet of material used to form the mesh (and therefore, the mesh itself) can be less than about 60 microns thick, or less than about 50 microns in thickness. Such dimension can facilitate a portion of the graft tissue to protrude above an upper surface of the mesh when the further mesh apparatus is pressed into the graft tissue. This exemplary configuration can facilitate formation of portions of tissue that may be used in an autografting procedure as described in more detail below.

The lateral widths or diameters of the mesh openings in this further exemplary mesh apparatus are preferably between about 100 microns and about 600 microns wide, or more preferably between about 200 microns and about 500 microns wide. The width of the mesh material between these openings is preferably small, e.g., less than about 100 microns. The width of the mesh material between the openings is preferably large enough to provide mechanical stability and not break or rupture when the further mesh apparatus is pressed into the graft tissue.

Figure 8B:
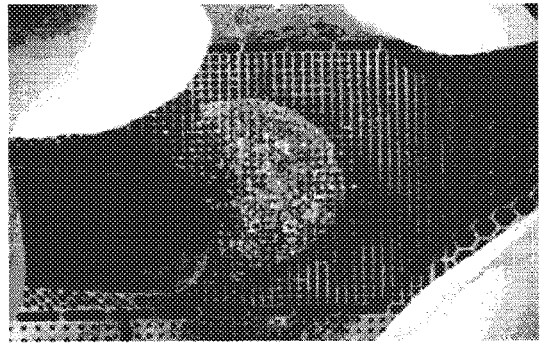
FIG. 8B is an image of the exemplary mesh apparatus of FIG. 8A being pressed onto the graft tissue to form micrografts.
Figure 9:
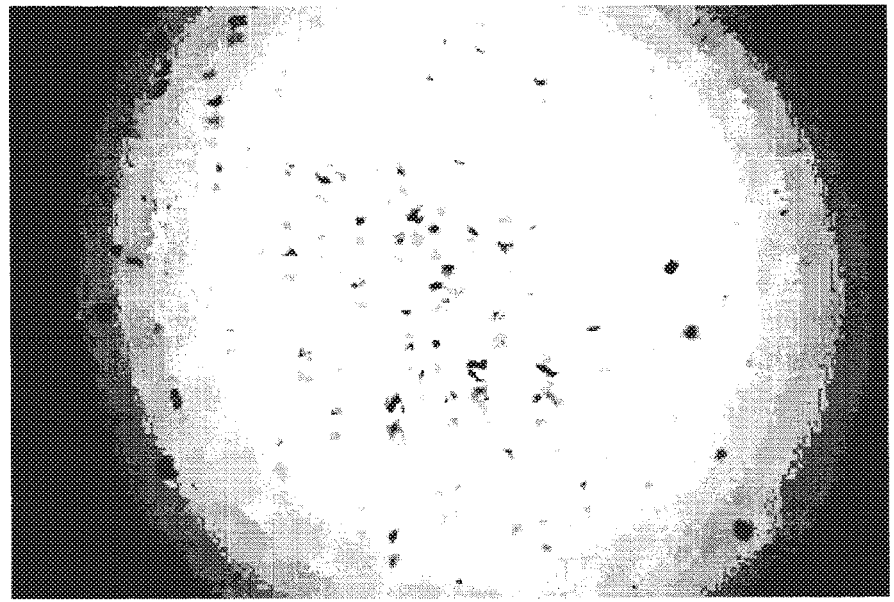
FIG. 9 is an image of a suspension of exemplary micrografts in solution.

The further mesh apparatus can be pressed onto the graft tissue as shown in FIG. 8B, such that a portion of the graft tissue protrudes above an upper surface of the mesh. A scraping device, e.g., a sharp blade or a steel scraper, may then be applied over the upper surface of the mesh to remove portions of the graft tissue protruding therefrom. These exemplary portions of removed tissue can be less than about 600 microns wide, or preferably less than about 400 microns wide, where these sizes correspond to the sizes of the openings in the mesh. For example, the average area of the portions of tissue can be between about 0.01 mm$^2$ and about 0.4 mm$^2$, or more preferably between about 0.04 mm$^2$ and about 0.25 mm$^2$. These exemplary sizes can be sufficiently small to provide good dispersion when suspended in a solution as described in more detail below, and large enough so that most of the portions of tissue generally contain at least one active melanocyte. The removed portions of tissue, shown in FIG. 9, can be used as micrografts for treating a damaged or depigmented area as described below. The actual size of these tissue portions may be somewhat smaller and/or irregular in shape based on the procedure of scraping portions of the tissue protruding from the mesh to form them.

Exemplary micrografts suitable for use with this method can also be formed by mechanical cutting of the epidermal graft tissue into micrografts having a size can be, e.g., between about 100 microns and about 600 microns in size. For example, a device that includes a plurality of closely-spaced blades, such as that shown in FIG. 3A, may be used as described herein. Alternatively, the exemplary mesh apparatus shown in FIG. 4A can be used to cut the graft tissue into individual micrografts. In these mechanical techniques, the stratum corneum of the graft tissue may be placed against the slide or other supporting surface. The cutting apparatus can then be pressed onto the upper portion of the graft tissue with sufficient force or pressure to produce cuts that pass substantially through the graft tissue, thereby forming individual micrografts having a size that can be less than about 400 microns.

These micrografts can then be suspended in a solution that can preferably be sterile and injectable. For example, a solution containing a small amount of glycerine (e.g., in a concentration of less than about 10%) may be used to help prevent adhesion of the micrografts to adjacent surfaces while maintaining viability of the micrografts. The solution can also include electrolytes (e.g., a saline solution) to help maintain viability of the micrograft tissue suspended therein. Other concentrations and solution components or additives can be used. In general, the solution can preferably be able to support viable micrograft tissue and be injectable into tissue without causing adverse reactions. The suspension containing the micrografts can be suctioned into a syringe.

For example, the suspension may be suctioned through a low-friction tube, e.g., a Teflon® tube, which is attached to the syringe to prevent adhesion of micrografts during the transfer of the suspension into and out of the syringe.

A suction blister can be formed in the depigmented area to be treated. In further exemplary embodiments, a plurality of suction blisters can be formed on the area to be treated, which may allow a larger area to be treated. Such exemplary blisters can be formed individually or as an interconnected network of blisters. For example, a plurality of elongated blisters such as those shown in FIG. 10A can be formed on the depigmented area to be treated. Alternatively, a plurality of intersecting elongated blisters may be formed, as shown in FIG. 10B. The square regions shown in FIG. 10B represent exemplary areas of undisturbed (unblistered or unraised) skin, whereas the network of substantially perpendicular intersecting lines represent raised portions of the epidermis formed by suction blisters.

As shown in FIG. 11, according to one exemplary embodiment, a needle 1100 (e.g., a 25G needle or the like) attached to a small syringe 1110 (e.g., a 1 cc syringe) can be inserted into the blister cavity 1120. The needle 1100 can be directed such that the needle tip enters the blister cavity 1120 through a lower surface 1130 and does not pierce the raised tissue 1140 covering the blister, as shown in FIG. 11. The micrograft-containing suspension in the syringe 1110 can then be injected into the blister cavity 1120, and the needle 1110 subsequently removed. The needle 1100 and an empty syringe 1110 can also be used to optionally drain the blister of fluid. The syringe 1110 can then be detached from the needle 1100, and a further syringe 1110 containing the solution with micrografts suspended therein can then be attached to the needle 1100, and the suspension injected into the drained blister.

The exemplary micrografts within the blister can then settle and attach to the tissue at the lower surface 1130 of the blister. The micrografts can contain healthy melanocytes and keratinocytes that can grow over the area being treated to promote healing and/or repigmentation of the skin tissue. Some cells provided in the portions of tissue prepared as described herein can undergo a de-differentiation process when transplanted, possibly due to cell signaling mechanisms. Such cells may then proliferate and subsequently differentiate into melanocytes when transplanted to recipient sites (e.g., within suction blisters or a wound dressing). Accordingly, the solution or dressing containing the portions of tissue can also include further additives known in the art that promote these effects (such as cell proliferation or differentiation) and can include the additives in a timed fashion to promote the different phases of proliferation, differentiation, etc.

By avoiding a puncture or piercing of the raised tissue 1140 over the blister, as shown in FIG. 11, the suspension containing the micrografts can be more easily retained within the blister cavity 1120. The intact raised tissue 1140 can also provide protection for the underlying skin to facilitate healing and reduce the risk of infection.

The exemplary patterns of blisters shown in FIGS. 10A and 10B include unraised portions of skin between the blisters. A small width of these unraised portions can be less than about 4 mm, or preferably less than about 2 mm, to facilitate a migration of melanocytes from beneath the raised blisters to the adjacent unraised portions. Accordingly, these exemplary unraised portions can be sufficiently small to result in an overall uniform pigmented appearance after the blisters heal.

If more uniform repigmentation is desired, a further pattern of blisters can optionally be formed over the same region of skin being treated, preferably after the previous blisters have healed. These additional blisters can be formed over areas of the region that were previously unraised/unblistered when the previous blisters were formed. These further blisters can then be drained and injected with a suspension of micrografts as described above, and allowed to heal. This exemplary procedure can be repeated until the desired degree of repigmentation and uniformity is achieved in the area being treated.

Other patterns of raised blisters can be used. Patterns of intersecting blisters, such as that shown in FIG. 10B, may be formed to facilitate distribution of the solution containing melanocytes throughout the 'network' of blisters using a single injection, such as that shown in FIG. 11 (or a small number of such injections provided at various locations within the blister network). The blisters can be gently massaged or palpated after injection of the solution containing the melanocytes to facilitate spreading of the melanocytes through the network of blisters. Other patterns of intersecting blisters that may be used include, e.g., triangular or hexagonal patterns, which can be formed as a plurality of elongated raised blisters that intersect at various angles.

The exemplary method described above can facilitate repair and/or repigmentation of skin tissue beneath blisters, while avoiding formation of open wounds on the area being treated. Further, the treated area can be many times larger than the size of the graft tissue removed from a donor site. Thus, larger areas of skin can be repaired or repigmented using a particular amount of graft tissue removed at donor sites.

In further exemplary embodiments of the present disclosure, the methods described herein can be applied to other tissues besides skin tissue, including other epithelial tissues such as lower GI tract for ulcerated tissue. Thus, grafts can be formed for various tissues that provide relatively little damage and rapid healing at a donor site while creating graft tissue suitable for repairing larger areas at recipient sites.

In a further aspect, exemplary embodiments of the present disclosure can provide an exemplary stretching apparatus 1200 that may be used to controllably stretch dressing material 1250 (e.g., Tegaderm™ dressing) having micrografts adhered thereto, as shown in FIGS. 12A-12D. The exemplary apparatus 1200 can be used to controllably increase the distances between the attached micrografts as described herein, for repairing or repigmenting larger areas of skin.

The exemplary stretching apparatus 1200 shown in FIG. 12A can include a housing 1210 having a closed end 1220 and an open end 1230. The housing 1210 may be substantially cylindrical, or other shapes may be used. The size and shape of the shell 1210 can be selected to provide an open end 1230 that can be of substantially similar size as, or larger than, the size of the dressing material 1250 (e.g., having micrografts adhered to) that is to be stretched. The housing 1210 and closed end 1220 can be provided together as a continuous structure that surrounds an interior volume and defines the opening 1230.

The dressing material 1250 can be placed over the open end 1230 of the stretching apparatus 1200, with the micrografts adhered to the outer surface of the dressing material 1250 (e.g., the side external to the interior of the stretching apparatus 1200). The dressing material 1250 can then be secured over the opening 1230, e.g., by using an O-ring 1260, an elastic band, or the like. A pressure source 1270 can be provided in communication with the interior volume of the shell 1210, optionally through a valve arrangement 1275. The pressure source 1270 and the valve arrangement 1275, for example, can be configured to provide and/or maintain a predetermined pressure within the interior volume of the exemplary stretching apparatus 1200. Alternatively, the pressure source 1270 and the valve arrangement 1275 can be configured to controllably increase the pressure in the interior volume of the stretching apparatus 1200 until a particular amount of stretching of the dressing material 1250 has occurred.

The pressure source 1270 can include, for example, an air pump (e.g., an electric pump or a hand pump). In one exemplary embodiment, the pressure source 1270 can be a tube that facilitates air to be blown into the interior volume of the stretching apparatus 1200 orally. In a further exemplary embodiment, the pressure source 1270 can include a canister enclosing a volume of compressed gas that may be controllably released into the interior volume of the stretching apparatus 1200 using, e.g., the valve arrangement 1275.

Pressure can be increased in the interior volume of the shell 1210, e.g., by forcing a gas or other fluid into the interior volume. This increased pressure can lead to an expansion of the dressing material 1250 over the open end 1230 of the stretching apparatus 1200. The pressure source 1270 can include a control arrangement configured to control the amount of stretching of the dressing material 1250. For example, a simple on/off switch may be used, with the amount of stretching manually controlled using the switch based on visual observation. The control arrangement may include a pressure display, and/or a pressure sensor connected to the valve arrangement 1275, such that a predetermined pressure can be provided within the interior volume of the shell 1210.

The exemplary stretching apparatus 1200 shown in FIG. 12A thus can facilitate a controlled amount of stretching of the dressing material 1250. The dressing material 1250 can be stretched substantially uniformly in different directions using the stretching apparatus 1200. Such stretching may not be uniform or omnidirectional if the dressing material is stretched using conventional techniques, e.g., if the edges of the dressing material 1250 are pulled in different directions by hand or by using a clamping device.

In a further exemplary embodiment, shown in FIGS. 12B and 12C, the exemplary stretching apparatus 1200 can further include a substrate 1280 affixed to a rod 1285. The substrate 1280 can be located within the interior volume of the stretching apparatus 1200. The rod 1285 may pass through an opening in the closed end 1220 of the apparatus 1200, or otherwise movably connected to the housing 1210, such that the position of the substrate 1280 can be varied relative to the open end 1230 of the housing 1210 by moving a proximal end of the rod 1285 that protrudes beyond a lower surface of the closed end 1220. A seal can be provided between the closed end 1220 and the rod 1285 that passes therethrough, where the seal is configured to maintaining an elevated pressure within the apparatus 1200, e.g., the seal may not allow a significant amount of gas to leak out through the opening in the closed end 1220, even when the rod 1285 is moved.

The interior volume of the exemplary stretching apparatus 1200 can be pressurized using the pressure source 1270 and/or the valve arrangement 1275, such that the dressing material 1250 having micrografts adhered thereto is stretched as shown in FIG. 12B. The substrate 1280 can be moved towards the stretched dressing material 1250 such that it contacts at least a portion of the dressing material 1250, as shown in FIG. 12C. Pressure within the interior of the apparatus 1200 can then optionally be released or reduced, e.g., using the valve arrangement 1275. The dressing material 1250 can then be trimmed or cut around the perimeter of the substrate 1280. This exemplary procedure can provide a portion of dressing material 1250 that is partially adhered to the substrate 1280 in a stretched or expanded state, as shown in FIG. 12D. A portion of the dressing material 1250 may be left protruding beyond the edges of the substrate 1280 to facilitate positioning and application of the expanded dressing material 1250 to an area of prepared skin to be treated as described herein. The rod 1285 can also be used as a handle to position the portion of dressing material 1250 over the area to be treated.

In a further aspect, exemplary embodiments of the present disclosure can provide a suction apparatus 1300 as shown in FIG. 13A, which can be used to form suction blisters in various configurations such as the exemplary blister network shown in FIG. 10B. A general suction blister device is described, e.g., in U.S. Pat. No. 6,071,247. The exemplary suction apparatus 1300 can include a vacuum source 1310. For example, the vacuum source 1310 can be a handheld pump which includes a pump body 1312 and a pair of spring-loaded handles 1316 that can be squeezed together one or more times to produce suction. Alternatively, the vacuum source 1310 can include, e.g., an electric pump or a vessel containing a heated volume of gas that is allowed to cool and contract.

The vacuum source 1310 can be provided in connection with a plate 1340 via tube 1330. One or more channels 1342 can be provided along the lower surface of the plate 1340. For example, a continuous network of such channels 1342 as viewed from the lower surface of the plate 1340 is shown in FIG. 13B. One or more conduits 1344 can be provided to form a passageway between the channel 1342 and an outer surface of the plate 1340. For example, at least one conduit 1344 can be provided for each separate channel 1342 in the block 1340. Each separate channel 1342 can then be used to form a separate suction blister. A pressure gauge 1320 can optionally be connected to the vacuum source 1310 to indicate the current pressure present between the tissue surface and the channel 1342.

The exemplary suction apparatus 1300 can be operated by placing the plate 1340 over the region of skin to be treated. A gel or other material can be provided on the lower surface of the plate 1340 to improve a seal between the plate 1340 and the skin surface. The region of skin can optionally be heated before the plate 1340 is applied, e.g., to a temperature up to about 45° C., or preferably between about 39 C-41 C. The heating can be performed using a conventional technique, such as contacting a warm object to the skin or exposing the skin to heated water or another fluid. Non-contact heating techniques and devices, e.g., heat lamps or infrared radiators, may also be used. Such heating can optionally be provided while the blister is being formed. The vacuum source 1310 can then be activated to produce a partial vacuum (e.g., a lower pressure) in the channels 1342. An appropriate low pressure can be maintained in the channels 1342 for a sufficient time to form suction blisters in the underlying skin, having the same pattern as the channels 1342. The time and pressure required to form suction blisters can be determined in accordance with conventional suction blister techniques. The time preferred to form such suction blisters can be reduced if the skin is preheated before application of the exemplary suction apparatus 1300.

The exemplary suction apparatus 1300 can facilitate a formation of a variety of patterns of suction blisters that can be shaped by appropriate design of the channels 1342. The lower surface of the block 1340 containing these channels 1342 can be provided in a variety of shapes, such as square (as shown in FIG. 13B), e.g., circular, oval, etc. for treating different regions of skin. The lower surface of the block 1340 may also be curved to more closely follow the contour of the region of skin being treated. For example, it may have a substantially cylindrical profile to conform to the curvature of an arm or a leg. The distance between adjacent channels may be less than about 4 mm, or preferably less than about 2 mm, to allow migration of melanocytes from beneath the formed blisters to the adjacent unraised portions, as described herein. A width of each channel can be less than about 10 mm wide, or less than about 5 mm wide. Such exemplary widths can form blisters that are large enough to provide a sufficient amount of blister area to be grafted to, while avoiding excessively large blisters that may take a long time to heal.

Figure 14:
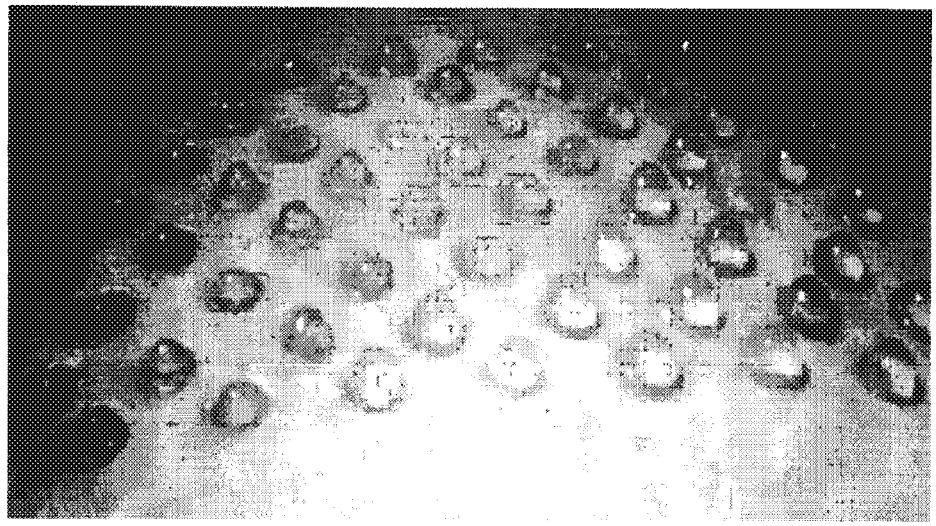
FIG. 14 is an exemplary image of a plurality of blisters formed at predetermined locations.

In a further aspect, exemplary embodiments of the present disclosure can provide an autografting method and apparatus in which a plurality of small spaced-apart grafts are formed at predetermined locations at a donor site and applied to a treatment site. For example, a plurality of small blisters, e.g., suction blisters or other raised portions of skin tissue, can be formed at a donor site as shown in FIG. 14.

Figure 15:
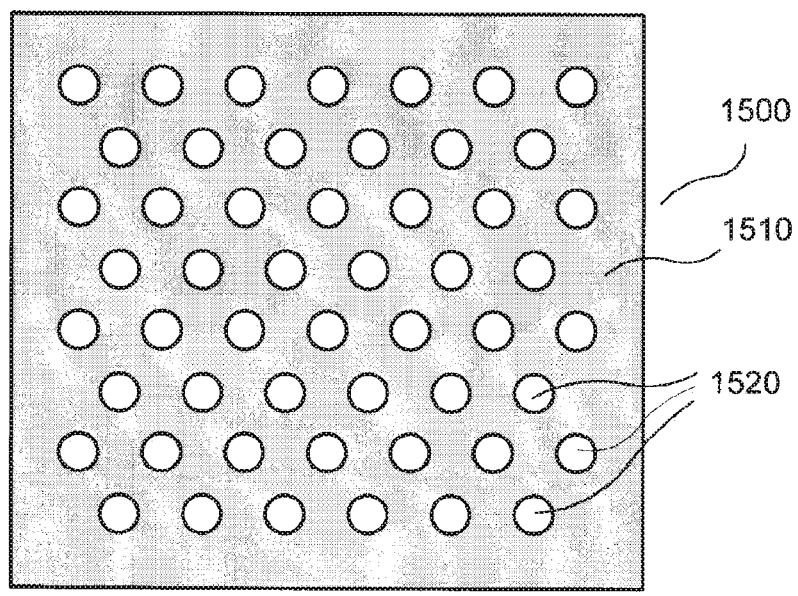
FIG. 15 is an illustration of an exemplary plate that can be used with an exemplary suction apparatus or the like to form the exemplary blisters shown in FIG. 14.

Such blisters can be formed, e.g., using an exemplary suction blister apparatus 1500 that can include a plate or sheet 1510 having a plurality of holes 1520 therethrough, e.g., as shown in FIG. 15. A width or diameter of each blister can be between about 0.5 mm and about 2.5 mm in diameter, which can provide graft tissue samples that are large enough to repair a large area of skin at a recipient site, while being small enough to facilitate healing after the graft tissue samples are removed from the donor site. Alternatively, larger or smaller blister sizes can also be used. The holes 1520 can be provided in any one of a variety of shapes. Holes that are substantially circular or ellipsoidal, e.g., having convex curved shapes, can be preferable to produce raised blisters having well-defined edges.

Figure 16A:
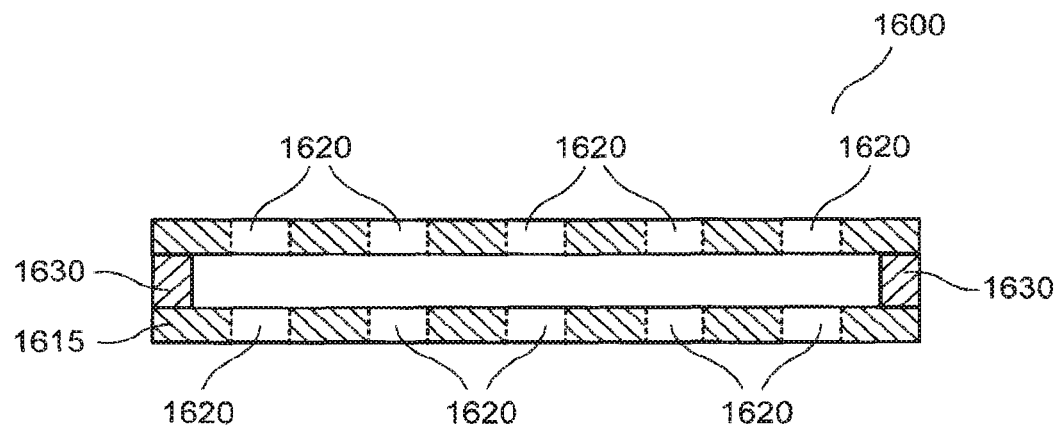
FIG. 16A is a side view of an exemplary apparatus that can be used to remove the raised portions of the plurality of blisters shown in FIG. 14 and facilitate their attachment to a dressing material.

An exemplary apparatus 1600, shown in FIG. 16A, can then be placed be over the plurality of blisters at the donor site. The exemplary apparatus 1600 shown in FIG. 16 can include an upper plate 1610 affixed to a lower plate 1615 such that a thin gap is provided between the plates, where the gap is sufficiently wide to allow a blade or other cutting edge to pass between the plates. For example, the plates 1610, 1615 can be affixed to each other using a plurality of spacers 1630 that can be provided at or near peripheral portions of the plates 1610, 1615. In certain exemplary embodiments, each of the plates 1610, 1615 can include a plurality of holes 1620 therethrough, where the pattern of holes 1620 can be substantially the same as or similar to that used to form the blisters. In further exemplary embodiments, the lower plate 1615 can be omitted, and the spacers 1630 can be configured to position the upper plate 1610 having the pattern of holes 1620 at a small distance away from the surface of the skin when the apparatus 1600 is placed over the formed blisters. In a still further exemplary embodiment, a vacuum source can be provided over the apparatus 1600 after it is placed on the skin, to form a plurality of blisters through the holes 1620.

The exemplary apparatus 1600 in FIG. 16A can then be placed over the blisters formed at the donor site, such that an upper portion of the blisters protrudes from the upper surface of the upper plate 1610 through the holes 1620. A dressing material, which can have adhesive properties on at least one side (e.g., Tegaderm™ dressing or the like), can then be applied over the upper plate 1610 and the protruding tops of the blisters, such that it at least partially adheres to the blisters. A blade or other cutting device can then be translated between the upper plate 1610 and lower plate 1620, or alternatively between the upper plate 1610 and the surface of the skin if no lower plate 1615 is provided, to sever the raised blisters from the underlying skin tissue. The dressing having raised portions of the blisters adhered thereto can then be removed from the upper plate 1610. In this exemplary manner, a pattern of small grafts formed from a plurality of blisters can be provided in predetermined locations on a dressing material.

Figure 16B:
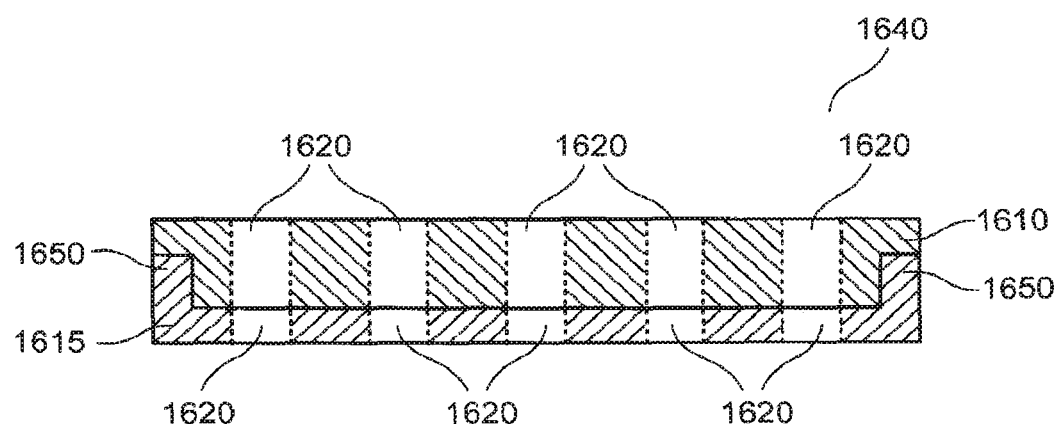
FIG. 16B is a side view of a further exemplary apparatus that can be used to remove the raised portions of the plurality of blisters shown in FIG. 14 and facilitate their attachment to a dressing material.

In a further exemplary embodiment, shown in FIG. 16B, an apparatus 1640 can be provided that includes a lower plate 1615 that can be slidably attached to the upper plate 1610, e.g., using protrusions 1650 that can slide within substantially parallel grooves provided in the upper plate 1610. The lower plate 1615 can be thin and/or provided with sharp edges around the holes 1620, such that the raised portions of the blisters can be severed from the underlying tissue by the edges of the holes 1620 in the lower plate 1615 when the lower plate 1615 is translated with respect to the upper plate 1610.

A plurality of blisters can be formed on a recipient site using the same technique described above for the donor site. The pattern or spatial arrangement of blisters can be substantially the same at both the donor and recipient sites. For example, each set of blisters can be formed using the same apparatus 1500 shown in FIG. 15 or a similar apparatus or article of manufacture. The blisters at the recipient site can be severed and discarded, or alternatively they can be affixed to a second piece of dressing material as described above with respect to the small blisters formed at the donor site.

The dressing material having the pattern of small grafts from the donor site adhered thereto can then be placed over the recipient site, such that the grafts are substantially aligned with the exposed areas where blisters were removed. The dressing can be left in place for a sufficient time to facilitate or allow the grafts to attach to the surrounding tissue (e.g., several days up to a few weeks), and the dressing material can then be removed. If the blisters from the recipient site are adhered to a second piece of dressing material (rather than discarded), this second piece of dressing material can be affixed over the donor site, such that the blisters removed from the recipient site substantially align with the exposed areas from the donor site where blisters were severed. This second dressing material can also be left in place until the blister pieces have sufficiently become attached to the surrounding tissue at the donor site.

In this exemplary manner, a plurality of separate, small grafts can be formed and removed from a donor site and positioned over corresponding exposed areas of skin at a recipient site. Optionally, the small pieces of tissue removed from the recipient site can also be positioned over matching exposed areas of skin at the donor site. After this exemplary autografting procedure is performed, most or all of the wounds and relocated pieces of tissue may be covered and dressed, such that they can proceed to heal.

In a still further exemplary embodiment, the recipient site can be prepared, for example, by removing at least a portion of the epidermis at the recipient site. Such preparation can be performed, e.g., using conventional dermabrading techniques. The dressing material having the small grafts from the donor site adhered thereto can then be placed over the recipient site, such that at least a portion of the grafts are aligned with areas of the recipient site where some or all of the epidermal tissue was removed. The dressing can be left in place for a sufficient time to facilitate or allow the grafts to attach to the surrounding tissue (e.g., several days up to a few weeks), as described above. Average distances between adjacent small grafts on the dressing material (which may correspond to the distance between the blisters formed at the donor site) can be selected based on migration of melanocytes and/or keratinocytes, as described above. For example, an average distances between nearest edges of adjacent small grafts can be less than about 4 mm, or less than about 2 mm, to facilitate migration of melanocytes between the small grafts. This average distance can be larger if keratinocytes migration is relevant to the tissue being treated, e.g., based on the greater typical migration distances of keratinocytes as compared with melanocytes.

Example [Note: This Section Describes Actual Procedures Formed, so No Further 'Exemplary' Language should be Inserted in this Section.]

An exemplary grafting procedure was performed in accordance with exemplary embodiments of the present disclosure, as described below in detail. The exemplary procedure was performed to provide repigmentation of a wrist area of a subject exhibiting depigmentation associated with vitiligo.

Figure 17A:
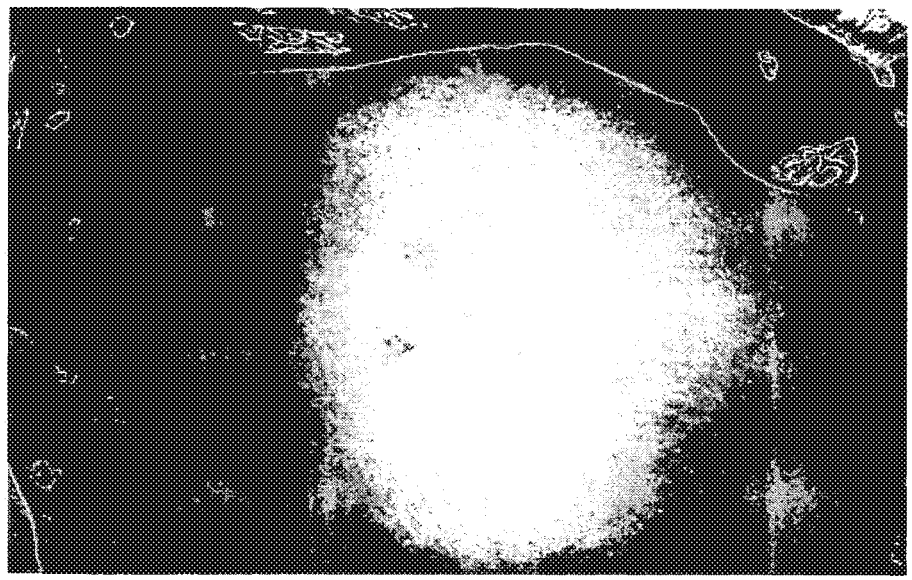
FIG. 17A is an exemplary image of a donor site six weeks after epidermal tissue from five blisters has been removed.

Five epidermal pieces of donor tissue were obtained in about one hour from the subject's thigh, aseptically, by forming suction blisters as described herein. The blisters were formed by heating the donor site to a temperature of about 41° C. and using a suction pressure of about 15 inches (½ atm.). Each piece of tissue obtained from a blister was about 8 mm in diameter. The donor site from which the five pieces of tissue were removed is shown in FIG. 17A, about six weeks after the blisters were formed. A small amount of hyperpigmentation (darkening) is visible where the epidermal tissue was removed. No dermal involvement or scarring was observed, and the mild hyperpigmentation may disappear within about 3-6 months.

Each of these pieces of epidermal graft tissue was then used to form a plurality of micrografts by pressing two stacked stainless steel meshes onto the outer (skin surface or stratum corneum) side of the graft using a mechanical press, as described herein. Each mesh was about 90 microns thick (corresponding to a stack having a total thickness of about 180 microns), with a width of each mesh line of about 100 microns. The holes in the mesh were about 400 microns wide. Using this exemplary procedure, a plurality of micrografts was formed from each piece of donor tissue, with each micrograft being about 400 microns wide. The micrografts were only partially separated from one another by the mesh apparatus, connected by small uncut portions of tissue, such that each piece of donor tissue could be handled as a single unit after forming the plurality of micrografts therefrom.

The five epidermal pieces of graft tissue were then placed on the sticky side of a piece of Tegaderm™ dressing (3M) as described herein, adjacent to one another, with the outer skin surface (stratum corneum) adhered to the Tegaderm™ dressing. This orientation facilitates direct contact between the keratinocytes and the melanocytes present in the graft tissue and the prepared surface of the recipient site, when the Tegaderm™ dressing is placed over the recipient site.

The Tegaderm™ dressing with the graft tissue adhered thereto was then affixed to the exemplary expansion device shown in FIG. 12A using an O-ring. A pump was used to increase the pressure within the expansion device and expand the Tegaderm™ dressing like a balloon, so as to stretch the dressing uniformly. This procedure resulted in a separation of adjacent micrografts as described herein. The individual micrografts did not appear to be stretched individually because of their small size and because the dead stratum corneum layer of each micrograft is adhered to the dressing, which does not directly contact live cells of the epidermis, allowing each micrograft to maintain its integrity.

The Tegaderm™ dressing was expanded such that a distance of about 2 mm between adjacent micrografts was formed without tearing of the stretched dressing. This corresponded to an area of dressing containing micrografts that was about 2.5 to 3 times the size of the donor site. A plastic ring was then adhered to the dressing just beyond the outer perimeter of the array of micrografts adhered to the dressing, to hold the dressing in a stretched configuration, and the outer portions of the dressing were then cut off around the ring. Another piece of unstretched Tegaderm™ dressing was then adhered to the non-sticky side of the stretched dressing to provide further strength and stability.

Figure 17B:
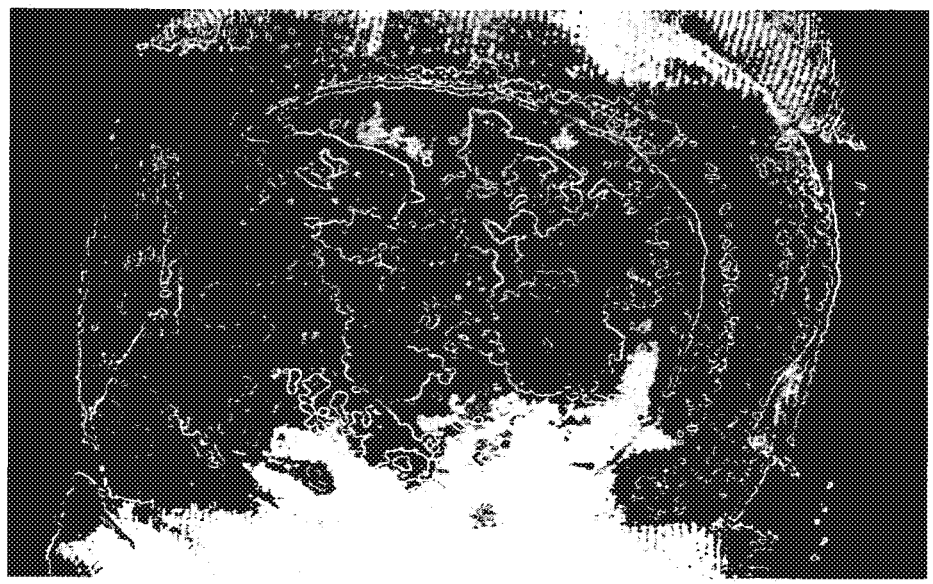
FIG. 17B is an exemplary image of a dermabraded recipient site covered with a dressing having a plurality of micrografts adhered thereto.

The recipient site was dermabraded using a conventional procedure, and kept moist. The stretched Tegaderm™ dressing having the separated micrografts adhered thereto, together with the unstretched Tegaderm™ dressing layer and plastic ring, was then placed onto the dermabraded recipient site. The unstretched Tegaderm™ dressing provided the outer surface of the dressing, away from the skin tissue. This dressing arrangement, including micrografts adhered thereto, is shown applied to the recipient site on the left wrist of the subject in FIG. 17B. The subject was then sent home with this dressing material held in place.

The dressing on the recipient site was changed after seven days. No antibiotics or pain killers were prescribed and they did not appear to be necessary. When the dressing was changed (seven days after the micrografts were applied to the recipient site), no repigmentation was observed. The recipient site appeared clean, with no evidence of infection or any other complication.

Two weeks after the micrografts were applied to the recipient site, first signs of repigmentation were visible in the form of multiple pigmented spots in the treated area, with no similar pigmented spots evident in the control and untreated areas. After six weeks, the pigmented macules coalesced to form larger pigmented patches. This observed behavior suggests that the micrografts were accepted and have exhibited expansion. FIGS. 17C and 17D show the recipient site before and six weeks after application of the micrografts as described herein. The height of the circled treatment area in these figures is about 3 cm. Much of the depigmented areas shown in FIG. 17C have become pigmented after six weeks, as shown in FIG. 17D, through attachment and growth of the applied micrografts.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention. All patents and publications cited herein are incorporated herein by reference in their entireties.

What is claimed is:
1. A tissue region effecting method comprising:
  removing a tissue sample from a site;
  separating the tissue sample into a plurality of micrografts;
  providing the plurality of micrografts on a material;

expanding the material to separate adjacent ones of the plurality of micrografts from one another by an average distance;

placing the material over the tissue region; and wherein said expanding the material to separate adjacent ones of the plurality of micrografts from one another includes (i) manually stretching the material or (ii) applying a pressurized gas to the material.

2. The method of claim 1, wherein an average area of the plurality of micrografts is between 0.0025 mm² and 1 mm².

3. The method of claim 1, wherein an average area of the plurality of micrografts is between 0.04 mm² and 1 mm².

4. The method of claim 1, wherein the average distance between adjacent ones of the plurality of micrografts on the material is less than 4 mm.

5. The method of claim 1, wherein the average distance between adjacent ones of the plurality of micrografts on the material is less than 2 mm.

6. The method of claim 1, wherein the tissue region is skin, and which includes removing epidermal tissue from at least a portion of the skin before placing the material over the skin.

7. The method of claim 1, wherein said providing of the plurality of micrografts on the material includes adhering the plurality of micrografts to the material.

8. The method of claim 1, which includes securing the material to an apparatus; and applying a manual force to the material secured to the apparatus.

9. The method of claim 1, wherein said separating the tissue sample into a plurality of micrografts includes forming indentations or cuts in the tissue sample.

10. The method of claim 1, where said providing the plurality of micrografts on the material includes adhering a stratum corneum of the plurality of micrografts to the material.

11. A tissue region effecting method comprising:
removing a tissue sample from a site;
separating the tissue sample into a plurality of micrografts;
providing the plurality of micrografts on a material;
expanding the material to separate adjacent ones of the plurality of micrografts from one another by an average distance;
placing the material over the tissue region; and
wherein said separating the tissue sample into a plurality of micrografts includes creating a substantially continuous tissue layer; and said expanding the material to separate adjacent ones of the plurality of micrografts from one another includes tearing portions of the substantially continuous tissue layer.

12. A tissue region effecting method comprising:
removing a tissue sample from a site;
separating the tissue sample into a plurality of micrografts;
providing the plurality of micrografts on a material;
expanding the material to separate adjacent ones of the plurality of micrografts from one another by an average distance;
placing the material over the tissue region; and
wherein said expanding the material to separate adjacent ones of the plurality of micrografts from one another includes stretching the material substantially uniformly in a plurality of directions.

13. A tissue region effecting method comprising:
removing a tissue sample from a site;
separation the tissue sample into a plurality of micrografts;
providing the plurality of micrografts on a material;
expanding the material to separate adjacent ones of the plurality of micrografts from one another by an average distance;
placing the material over the tissue region; and
wherein said expanding the material to separate adjacent ones of the plurality of micrografts from one another includes (i) securing the material to a stretching apparatus and (ii) applying a positive air pressure to a surface of the material.

14. The method of claim 13, wherein said applying the positive air pressure includes increasing the air pressure in a sealed environment until the air pressure reaches a predetermined pressure.

15. A material expanding system comprising:
a housing defining (i) an opening and (ii) an air pressure inlet;
a material secured over the opening of the housing so that the housing and the material define an interior volume;
a plurality of micrografts coupled to the material; and
an air pressure source coupled fluidly with the air pressure inlet of the housing, the air pressure source configured to supply air pressure to the interior volume of the housing through the air pressure inlet such that the air pressure expands the material secured over the opening and separates adjacent ones of the plurality of micrografts from one another by an average distance.

16. The system of claim 15, which includes an O-ring, the O-ring coupled to the material and the housing so as to secure the material over the opening of the housing.

17. The system of claim 15, which includes at least one valve configured to selectively allow positive air pressure from the air pressure source to be supplied through the air pressure inlet to the interior volume.

18. The system of claim 15, wherein the system is configured such that the air pressure expands the material substantially uniformly in a plurality of directions.

19. The system of claim 15, wherein the material includes a biocompatible film.

20. The system of claim 15, (i) wherein the opening is a first opening, and wherein the housing defines a second opening opposite the first opening, and (ii) which includes a rod structured and arranged to be (a) received through the second opening and (b) moveable within the interior volume so that the rod can contact a surface of the material secured over the opening.

21. The system of claim 20, wherein the second opening includes a seal structured and arranged to allow the rod to move within the second opening while maintaining a substantially air tight seal within the interior volume.

22. The system of claim 15, wherein the system is configured such that when the material expands, the average distance between adjacent ones of the plurality of micrografts is (i) less than about-2 mm or (ii) less than 4 mm.

23. The system of claim 15, wherein the material is adhered to the plurality of micrografts.

24. The system of claim 15, wherein the plurality of micrografts include a substantially continuous tissue layer, and the air pressure tears the substantially continuous tissue layer.

* * * * *

UNITED STATES PATENT AND TRADEMARK OFFICE
CERTIFICATE OF CORRECTION

PATENT NO. : 10,278,724 B2
APPLICATION NO. : 15/253525
DATED : May 7, 2019
INVENTOR(S) : Falguni Asrani et al.

It is certified that error appears in the above-identified patent and that said Letters Patent is hereby corrected as shown below:

In the Claims

Column 22, Claim 13, Line 3, "separation" should be --separating--.

Column 22, Claim 22, Line 57, "about-2" should be --2--.

Signed and Sealed this
Twenty-fifth Day of June, 2019

Andrei Iancu
*Director of the United States Patent and Trademark Office*